US00PP34006P2

(12) United States Plant Patent
Caratan

(10) Patent No.: US PP34,006 P2
(45) Date of Patent: Mar. 15, 2022

(54) GRAPEVINE PLANT NAMED 'PROSPERITY SEEDLESS'

(50) Latin Name: *Vitis vinifera*
Varietal Denomination: Prosperity Seedless

(71) Applicant: C&M International, LLC, Olympia, WA (US)

(72) Inventor: Anton G. Caratan, Bakersfield, CA (US)

(73) Assignee: C&M International LLC, Delano, CA (US)

( * ) Notice: Subject to any disclaimer, the term of this patent is extended or adjusted under 35 U.S.C. 154(b) by 0 days.

(21) Appl. No.: 17/097,251

(22) Filed: Nov. 13, 2020

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207, 206, 205
CPC ..... A01H 5/0812
See application file for complete search history.

(56) References Cited

U.S. PATENT DOCUMENTS

PP17,504 P3 3/2007 Maranto

*Primary Examiner* — Kent L Bell
(74) *Attorney, Agent, or Firm* — Buchanan Ingersoll & Rooney P.C.

(57) ABSTRACT

A branch mutation of the 'Blanc Seedless' (*Vitis vinifera*) grapevine named 'Prosperity Seedless' is disclosed. 'Prosperity Seedless' is distinguished over the known variety of 'Blanc Seedless' by its larger, more elongated fruit size.

3 Drawing Sheets

Genus and species: *Vitis vinifera.*
Variety denomination: 'Prosperity Seedless'.

STATEMENT REGARDING FEDERALLY SPONSORED RESEARCH OR DEVELOPMENT

Not applicable.

BACKGROUND AND ORIGIN OF THE NEW VARIETY

The present new cultivar relates to a naturally occurring sport of an unnamed branch mutation of the 'Blanc Seedless' grapevine (U.S. Plant Pat. No. 17,504), which will hereinafter be denominated as 'Prosperity Seedless', and, more particularly, to a grapevine which produces a large, elongated, vigorous and firm fruit of which is mature for commercial harvesting and shipment in mid-September to mid-October in the San Joaquin Valley of central California.

The new grapevine cultivar possesses many of the attractive characteristics of prior commercially successful varieties, while possessing a distinctive quality which makes it uniquely appealing for commercial harvesting and shipment.

ORIGIN AND ASEXUAL REPRODUCTION OF THE NEW VARIETY

The parent plant is an unnamed branch mutation of grapevine 'Blanc Seedless', and the new cultivar is a naturally occurring sport of the unnamed branch mutation. The new cultivar, 'Prosperity Seedless', was discovered by the inventor approximately ⅛th mile south of avenue 24 and ⅜ths of a mile east of Road 136 in Delano, Calif. on Oct. 10, 2018. The grapevine of the present invention is a naturally occurring sport of an unnamed branch mutation of the 'Blanc Seedless' variety. The newly discovered cultivar is evidenced in that the fruit produced therefrom is larger and more elongated when compared to the fruit of the 'Blanc Seedless' grapevine and of the unnamed branch mutation.

In 2019, the vine was observed to see if it would produce the same elongated fruit that it did in 2018. Wood was harvested from the new cultivar and grafted onto 'Freedom' rootstock (not patented) in 2019. In 2020, fruit was observed during development and was harvested at harvest time. The fruit was compared to that of the new cultivar. The inventor confirmed that, in all respects, the fruit was identical to the fruit produced in 2018.

'Prosperity Seedless' has been asexually reproduced through a vegetative cutting, which was shown to stably produce the unique features of the new cultivar in successive generations of asexual propagation, and fruit was harvested from the cutting in 2020. The new fruit from the asexual reproduction was identical to the fruit produced in 2018 and 2019.

SUMMARY OF THE NEW VARIETY:

The new grapevine cultivar denominated 'Prosperity Seedless' is characterized by producing larger, more elongated, generally white, or light green, seedless berries when compared to other varieties, including 'Blanc Seedless'. Specifically, the berries of 'Prosperity Seedless' are 2.0 to 2.5 inches long and have a diameter between 0.75 to 0.88 inches; whereas the 'Blanc Seedless' variety produces berries that are 0.8 to 1.3 inches long and have a diameter of 0.6 to 0.9 inches. The berries of 'Prosperity Seedless' are ripe for commercial harvesting and shipment in approximately mid-September thru mid-October in the San Joaquin Valley of central California. The new cultivar is most closely similar to the 'Blanc Seedless' grapevine, but is distinguished therefrom by its fruit size and shape. The fruit is firm, has a mild flavor, good eating quality and an apparent resistance to adverse conditions. While the organoleptic qualities, flavor and crunch of the fruit from 'Prosperity Seedless' is similar to the fruit of 'Blanc Seedless', the density of the clusters of 'Prosperity Seedless' are less dense than those of 'Blanc Seedless'.

Moreover, the new variety can be readily distinguished from non-parental related similar varieties. The closest non-parental comparison cultivar is the 'Thompson Seedless' (not-patented), which is similar to the new cultivar in that it has no seeds and is green in color like the 'Prosperity Seedless', but is harvested about a month earlier and does not have the desirable organoleptic qualities, flavor and crunch of 'Prosperity Seedless'.

BRIEF DESCRIPTION OF THE PHOTOGRAPHS

The accompanying photographic drawings show typical fruit and foliage characteristics of the 'Blanc Seedless' and 'Prosperity Seedless' grapevine varieties with colors being as true as possible with illustrations of this type.

The photographic drawing of FIG. 1 shows the typical foliage and fruit size of the 'Blanc Seedless' grapevine variety.

The photographic drawings of FIG. 2 and FIG. 3 show the larger, more elongated fruit size of the 'Prosperity Seedless' grapevine at 13 years old.

DETAILED BOTANICAL DESCRIPTION

Referring more specifically to the botanical details of this new and distinct cultivar of grapevine, the following has been observed under the ecological conditions prevailing at the vineyard of origin which is located near Delano, Calif. All major color code designations are by reference to the Dictionary of Color, by Maerz and Paul. Common color names are also occasionally employed.

The new cultivar of the subject invention was selected by the inventor approximately ⅛th mile south of avenue 24 and ⅜ths of a mile east of Road 136 in Delano, Calif. The new cultivar was 13 years old when discovered. The new cultivar was on 'Thompson Seedless' grapevine root stock and observed in 2019 to see if it would produce the same fruit as it did in 2018. And, fruit on an asexual reproduction was observed in 2020. Further characteristics of the new cultivar are detailed as followed.

Vine:

*Generally.*—Size. — Large. Appearing as a bush. Typical observed plant height 5 feet to 6 feet and plant diameter 5 feet to 6 feet, both subject to pruning and training. Some of the canes extend to 2.5 meters (8 feet) and the canes can be trained on high trellises. Vigor. — Vigorous. More vigorous than 'Blanc Seedless'. The canopy is thick. Productive capacity. — Very productive with spur pruning. Tendency to produce a small secondary crop on current season's growth. Produces about 40 kg of fruit each year since 2018. Trunk: fibrous and striated. Size. — Slender. Long split straps. Typical and observed trunk diameter at one foot height from ground, 59 millimeters (2.3 inches). Color. — Bark — Thrush Shag Bark (14-C-7) — under bark — Copper Brown (6-C-12). Canes. — Medium length and width (16-20 nodes). Some canes are long to 2.5 meters (8 feet). The width at the 3rd node is 11 millimeters (0.4 feet). Smooth texture. Mature canes. — Color — Raw Sienna (13-L-10). Nodes. — Round, slightly enlarged. Lengths between the nodes is 76.2 millimeters (3 inches) to 127.0 millimeters (5 inches). Shoots. — Size — Medium to long. Shoots. — Length — 76.2 millimeters (3 inches) to 101.6 millimeters (4 inches). Shoot diameter 0.7 millimeters. Shoots are slightly colored, Verdant Green 20-K-5 with Concord 45-L-1 stripes at the base when in close proximity, color of base changes to Verdant Green 20-K-5 when proximity to shoot increases, with a glossy appearance. Shoots. — Shape — Circular to slightly flat. Shoots. — Contour — Smooth. Tendrils. — Numbers — 8 per shoot (average). Tendrils. — Width — 3.2 mm ($1/8^{th}$) of an inch. Tendrils. — Color — Verdant Green 20-K-5. Tendrils. — Length — 101.6 millimeters (4 inches) to 203.2 millimeters (8 inches). Tendrils. — Location — Discontinuous. Tendrils. — Form — Bifurcated and trifurcated. Tendrils. — Texture — Smooth. Buds. — Shape — Conical, slightly pointed. Buds. — Size — Medium. Average length 6 millimeters. Average width 6 millimeters. Buds. — Fruitfulness — Base mostly fruitful. Buds. — Color — Verdant Green 20-K-5. Bud break. — Near Delano, in the San Joaquin Valley of central California, in the end of March.

Leaves:

*Size.*—Generally — Medium to large.

*Density.*—Heavy.

*Average length.*—Mature Leaf — 101.6 millimeters (4 inches) to 152.4 millimeters (6 inches).

*Average width.*—Mature Leaf — 127 millimeters (5 inches). Five lobes, basal lobe short, less prominent than laterals. Terminal teeth large in contrast with lateral teeth. Petiole sinus wide opened, "U" shaped, occasionally overlapping inferior sinuses. Inferior sinuses narrow.

*Texture.*—Upper Surface — Smooth.

*Texture.*—Lower Surface — Glabrous.

*Color.*—Dorsal — Brewster green (24-L-7).

*Color.*—Ventral — Cypress green (23-L-7).

*Color.*—Leaf Vein — Midrib — Grape green (21-J-1).

*Petiole.*—Length — 76.2 millimeters (3 inches) to 127.0 millimeters (5 inches), round or flattened.

*Petiole diameter.*—Thin, $1/8^{th}$ of an inch.

*Petiole color.*—Verdant Green 20 K-5 with lines and areas of Concord 45-L-1.

*Petiole sinus.*—Form — U shaped, lateral sinus occasionally overlapping.

*Petiole texture.*—Smooth.

*Lobe.*—Four pointed.

*Marginal form.*—Generally — Serrate, 10 to 14 per lobe.

*Teeth.*—Size — Irregular.

*Teeth.*—Number — 50 to 60.

*Teeth.*—Shape — Pointed.

Inflorescence:

*Size.*—Medium.

*Length.*—4" to 6".

*Width.*—3" to 4".

*Number borne per spur.*—Average two.

*Number borne per vine.*—30 to 35 (16 spurs).

Flowers:

*Flowers.*—Location — (Node where fruit is p roduced.) — Usually 2nd to 4th node from the base on spur pruning. Flower, still closed, is pear shaped.

*Type.*—Fertile.

*Pedicel.*—Adherence to berries — strong.

*Pedicel diameter.*—$2/32^{nds}$ of an inch to $3/32^{nds}$ of an inch.

*Pedicel color.*—Verdant Green 20-K-5.

*Length.*—7 millimeters to 8 millimeters.

*Diameter.*—$2/32^{nds}$ of an inch to $3/32^{nds}$ of an inch.

*Number of clusters per vine.*—30 to 35. Microscopic bud examination indicates that six percent (6%) of the buds have double cluster primordia the size of peduncle. Medium length, 50 millimeters (2 inches). Average width 5 millimeters (3/16 inch).

*Date of bloom.*—May 5.

*Date of full bloom.*—May 10 to May 12.

*Date of visible berries set.*—May 18.

*Stamens.*—Upright or diverging. Numbers — 6. Stamens length 1.6 millimeters, filaments straight.

*Length of filaments.*—Average 2 millimeters.

*Petals and sepals.*—Number 5. Sepals poorly developed.

*Color.*—(22-L-4) Calla green. They are formed like a cap and at bloom the petals open from the bottom to the top from the pressure of the stamens and, after, stay at the top like an inverted cup and later drop.

*Pistils.*—Color — (22-L-4) Calla green.

*Pistils.*—Number per flower — One small pistil which produces a liquid to hold pollen grains to favor germination.

*Amount of pollen.*—Abundant.

*Pollen.*—Color — Reed Yellow (10-I-1).

Fruit:

*Maturity when described.*—Ripe for commercial harvesting and shipment approximately mid-September thru mid-October near Delano, in the San Joaquin Valley of central California, about four weeks later than the 'Thompson Seedless' (not-patented) grapevine and two to three weeks later than 'Red Globe' grapevine (U.S. Plant Pat. No. 4,787) and two weeks earlier than 'Crimson' grapevine (not-patented).

*Solids.*—Sugar — 18.0%.

*Acid.*—Percent titratable acidity 0.46% (Oct. 1, 2020.).

*Sugar/acid ratio.*—39.1.

*Juice ph.*—3.57 on Oct. 1, 2020.

*Seeds.*—None. Seedless.

*Pedicel.*—Strong.

*Berry.*—Weight — 6 grams (0.21 ounces) to 8 grams (0.28 ounces).

*Juice color.*—Colorless.

*Cluster.*—Generally — Medium to large.

*Cluster size.*—Length from the point of attachment averages 304 millimeters (12 inches). Cluster size itself averages 127-152 millimeters (5" to 6" inches) in width and 228-279 millimeters (9" to 11" inches) in length.

*Cluster.*—Weight — Average one pound.

*Compactness.*—Loose to compact.

*Cluster.*—Form — Conical shouldered.

*Berry.*—Size — Medium to large.

*Berry.*—Form — Mostly uniform.

*Berry.*—Size — Dimensions Longitudinal Axis — 50.8 millimeters (2.0 inches) to 63.5 millimeters (2.5 inches).

*Berry.*—Size — Diameter Axis — 19 millimeters (0.75 inches) to 23 millimeters (0.88 inches).

*Berry.*—Numbers — 100 to 140 per cluster.

*Form.*—Ellipsoidal elongated.

*Thickness.*—Smooth, thick and resistant to detachment.

*Texture.*—Firm.

*Tendency to crack.*—None.

*Color.*—Mignon green (21-K-2) and amber yellow (10-J-3) on exposed berries.

*Pulp.*—Adheres to skin.

*Lenticels.*—One small, round pore like in distal end.

*Flavor.*—Sweet, mild to neutral.

*Texture.*—Crisp, firm.

*Color of flesh.*—Love Bird 18-L-6.

*Eating quality.*—Good.

*Use.*—Dessert.

*Keeping quality.*—After two months in the storage, still in good appearance.

*Resistance to disease.*—Resistant to powdery mildew.

*Resistance to.*—Cold, drought, heat and wind. The new variety is well adapted to the type of soil and climatic conditions of the central valley of California where most of the table grapes in California are grown. The minimum and maximum temperatures range from 25° Fahrenheit to 108° Fahrenheit. Late spring fronts are rare in the central valley of California.

*Shipping and handling qualities.*—Untested.

Although the new variety of grapevine possesses the described characteristics noted above as a result of the growing conditions prevailing near Delano, in the central part of the San Joaquin Valley of California, it is to be understood that variations of the usual magnitude and characteristics incident to changes in growing conditions, irrigation, fertilization, pruning, pest control, climatic variations and the like are to be expected.

I claim:

1. A new and distinct grapevine named 'Prosperity Seedless' as illustrated and described herein.

* * * * *

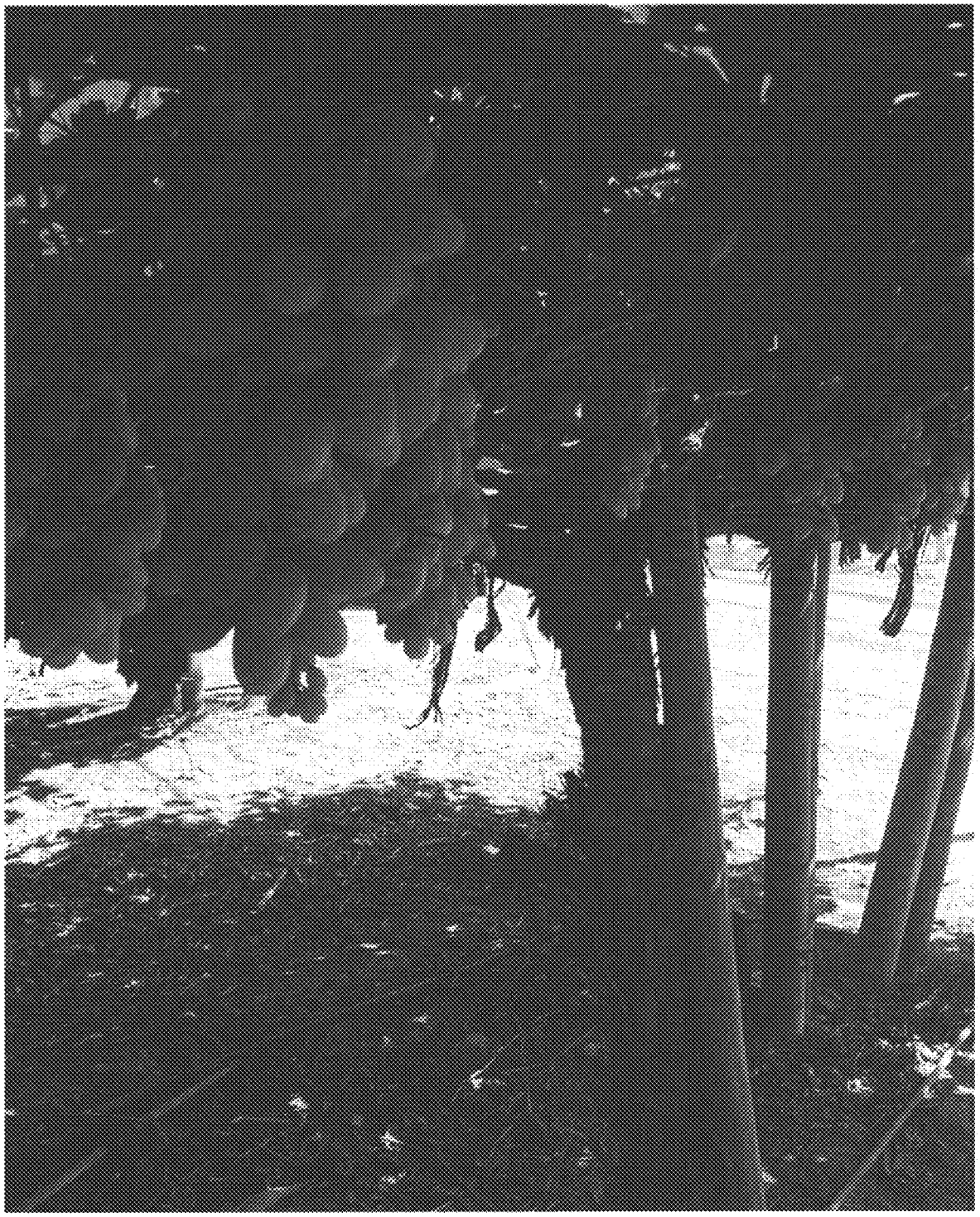
FIG. 1 'Blanc Seedless'

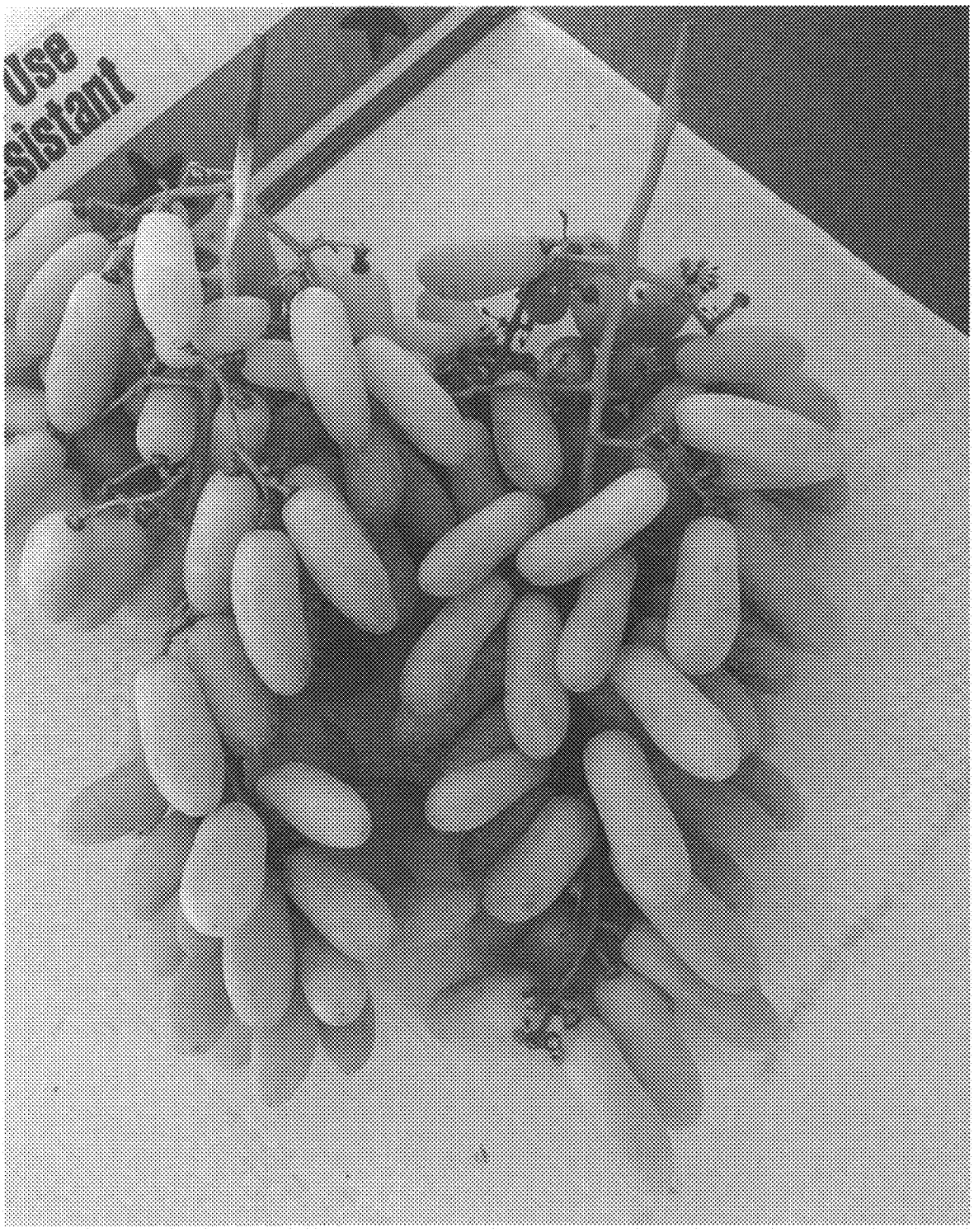
FIG. 2 'Prosperity Seedless'

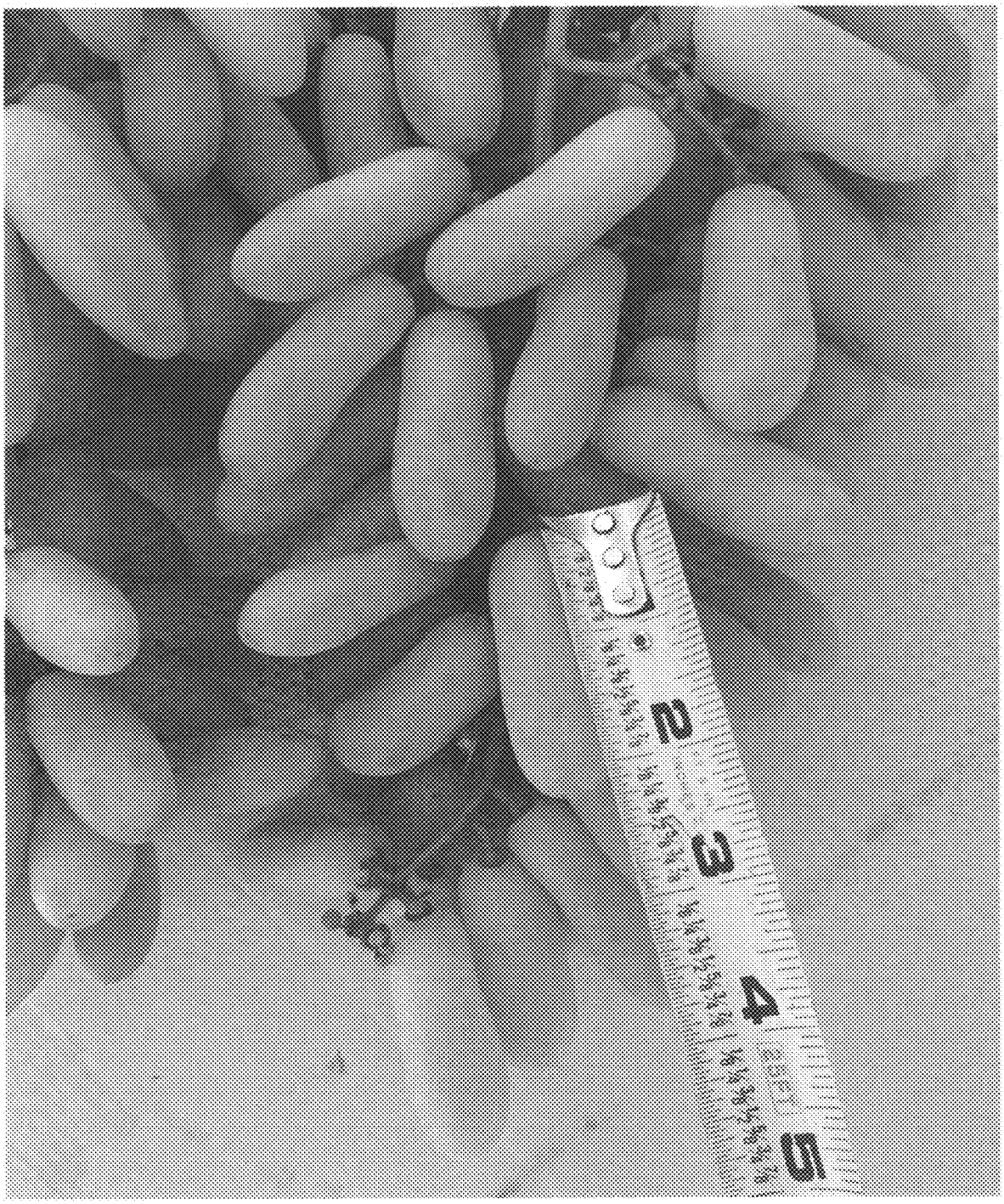
FIG. 3 'Prosperity Seedless' with Fruit Measurement